United States Patent [19]

Pinchuk

[11] Patent Number: 5,152,776
[45] Date of Patent: Oct. 6, 1992

[54] BALLOON INFLATION DEVICE

[75] Inventor: Leonard Pinchuk, Miami, Fla.

[73] Assignee: Cordis Corporation, Miami Lakes, Fla.

[21] Appl. No.: 793,500

[22] Filed: Nov. 15, 1991

Related U.S. Application Data

[63] Continuation of Ser. No. 504,328, Apr. 3, 1990, abandoned.

[51] Int. Cl.⁵ ............................................. A61M 29/02
[52] U.S. Cl. ................................. 606/192; 606/194; 604/97; 604/99
[58] Field of Search ................. 606/192, 194; 604/96, 604/97, 98, 99

[56] References Cited

U.S. PATENT DOCUMENTS 3,798,431  3/1974  Schulkind et al. .
4,439,186  3/1984  Kuhl ....................................... 604/99
4,702,393  10/1987  Chen .
4,872,483  10/1989  Shah ................................. 604/99 X

FOREIGN PATENT DOCUMENTS 2801528  4/1979  Fed. Rep. of Germany ...... 606/194

*Primary Examiner*—Michael H. Thaler
*Attorney, Agent, or Firm*—Lockwood, Alex, Fitzgibbon & Cummings

[57] ABSTRACT

A balloon inflation device is provided by which fluid conditions, such as pressure, developed within a known angioplasy balloon may be controlled according to a predetermined pattern. Actual fluid conditions developed within the balloon are identified by a monitor included within the invention and are communicated to a microprocessor from which, when appropriate, corrective orders are sent to the drive mechanism.

8 Claims, 2 Drawing Sheets

BALLOON INFLATION DEVICE

This application is a continuation of application Ser. No. 504,328, filed Apr. 3, 1990, now abandoned.

BACKGROUND AND DESCRIPTION OF THE INVENTION

The present invention generally relates to balloons useful as medical devices, as well as the procedure utilizing the same. More particularly the invention relates to medical or surgical balloons, and to catheter assemblies incorporating them that are useful in dilating blocked vasculature and other body passageways through the intraluminal expansion of the balloon. With the apparatus and method of the present invention, a balloon positioned at the site of the blockage may be inflated and deflated according to a programmed pattern thereby obviating the prolonged total cessation of blood flow to distal sites as in conventional balloon catheter devices.

Angioplasty is one therapeutic approach by which blocked vascular tissue may be opened. In balloon angioplasty, a practitioner typically positions a deflated and collapsed balloon, affixed near or at a distal end of a catheter, at the partially or nearly wholly occluded area of the vessel. The practitioner manually inflates the balloon thereby applying pressure to the intraluminal surface of the vascular blockage. The obstructing material is compressed against the walls of the afflicted vessel and, as is often the case, the vessel wall is stretched and the capsule surrounding the vessel torn. Upon deflating the balloon, an enlarged opening results through which blood may flow freely again. The procedure advantageously obviates the need for surgical methods which expose, incise, remove, replace or bypass the deficient blood vessel.

The conventional approach to balloon angioplasty relies heavily on the practitioner's manual dexterity and experience. To illustrate, the procedure typically requires the practitioner to estimate the rate at which the balloon must be manually expanded. If, for example, the practitioner estimates that the blockage may be particularly responsive to a quick compressive force, the practitioner may expand the balloon at a rapid rate. The procedure requires also the practitioner to estimate the optimal maximum pressure to which the balloon must be manually inflated. Because some stenoses, such as atherosclerotic plaque, are generally compression-resistant, the practitioner may decide to inflate the balloon to a greater maximum pressure level. Additionally, this procedure requires the practitioner to estimate the length of time a given pressure must be maintained in order to effect the proper degree of dilatation. Some tissue may not dilate in response to a quick compression force.

The major drawback associated with the conventional approach to balloon angioplasty is that it is an empirical art, that, because the response to the varying rate, maximum pressure, and length of inflation time is not altogether predictable, produces inconsistent and often times unexpected and potentially dangerous results. For example, if the practitioner inflates the balloon at too rapid of a rate or to too high of a pressure, the balloon and the afflicted vessel may rupture. Inflating the balloon to a moderate pressure level to avoid a rupture may create a different set of problems. Because even a moderately-pressurized balloon typically blocks the flow of blood to areas distal to the treatment site, coronary pressure in the distal region resultingly falls off. In the case of percutaneous transluminary coronary angioplasty, the lack of blood flow past the inflated balloon deprives the heart muscle of oxygen; eschemia results. Patients generally begin to complain of the associated pain after twenty seconds. However, ninety seconds is the maximum amount of time the flow of blood can be completely blocked. At this point, the pain becomes unbearable and the risk of eschemia-related cardiac infarction is extremely high.

Accordingly, prior to the development of the present invention, there was a demand in the art for an apparatus and method by which vascular passageways may be opened in a more controlled and less empirical manner. Specifically, there was a demand for an apparatus and method by which balloon angioplasty may be performed that did not have the associated prolonged stoppage of blood flow to sites distal to the treatment site. For example, by such a preferred apparatus and method the balloon could be inflated and deflated in rapid succession for a period of four minutes—instead of a continuous inflated period of ninety seconds—to allow for intermittent blood flow past the balloon. The present invention fills the demand.

An improved balloon inflation device is provided which includes a drive mechanism by which pump means can be actuated in order to deliver or remove a volume of fluid to or from an angioplasty balloon of a known amount and according to a pre-determined pattern. The actual fluid conditions present in the balloon and the catheter, to one end of which the pump means is attached and to the other general end of which the balloon is attached, are automatically quantified by a monitoring means included with the drive mechanism and communicated to a microprocessor. Besides including sufficient logic to operate the drive mechanism, the microprocessor includes programmed logic by which data regarding the actual fluid conditions developed within the balloon is compared to a set of expected conditions. Deviations from the pre-determined pattern, such as caused by fluid leakage from the catheter and/or angioplasty balloon, are automatically corrected by appropriate orders developed by the microprocessor and communicated to the drive mechanism. Furthermore, the drive mechanism may include logic by which the volume of the balloon and the pressure within it may be compared in order to determine the actual radial change of the balloon. The feature is especially advantageous for compliant balloons.

Accordingly, it is a principal object of the present invention to provide a new apparatus and method with which to perform percutaneous transluminal coronary angioplasty (PTCA), as well as other dilatation procedures.

A further object of the invention is to provide a new apparatus and method by which a balloon included with a PTCA catheter assembly and specifically the balloon's expansion and contraction may be more finely controlled.

Another object of the invention is to provide a new apparatus and method in which the pressure within, and thereby the external dilative force applied by an angioplasty balloon or the like is controlled according to programmed logic.

An additional object is that the control of the expansion and contraction of the angioplasty balloon is provided by programmed logic contained within a microprocessor through control of the drive mechanism of the present invention.

These and other objects, features and advantages of this invention will be more clearly appreciated and understood through a consideration of the following detailed description.

BRIEF DESCRIPTION OF THE DRAWINGS

In the course of the description, reference will be made to the attached drawings, wherein.

DESCRIPTION OF THE PARTICULAR EMBODIMENTS

Figure 1:
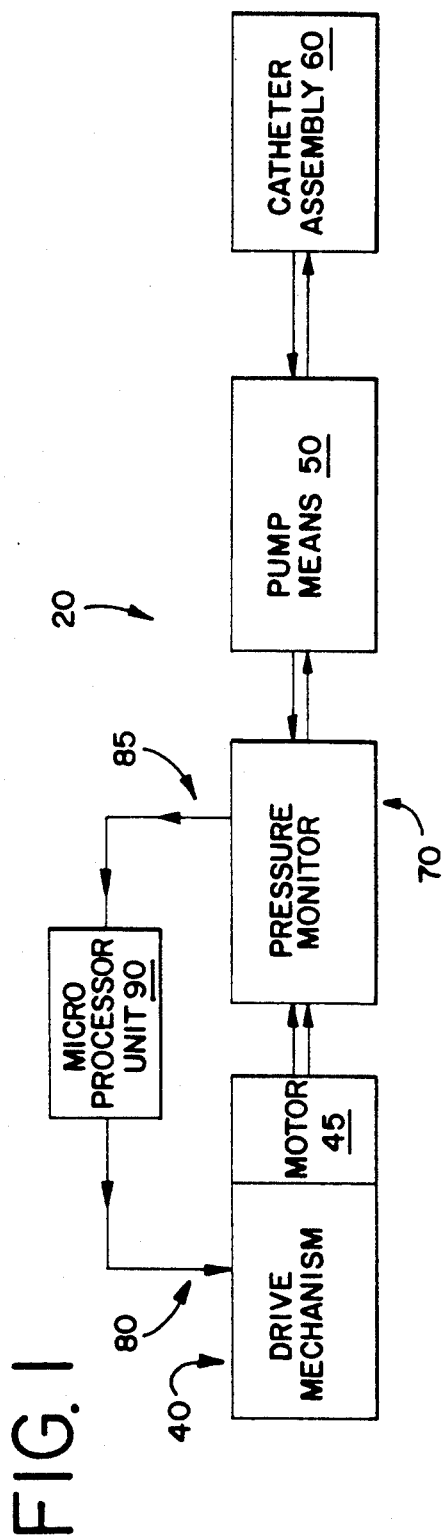
FIG. 1 is a schematic representation of an apparatus according to and used to effect the present invention.
Figure 2:
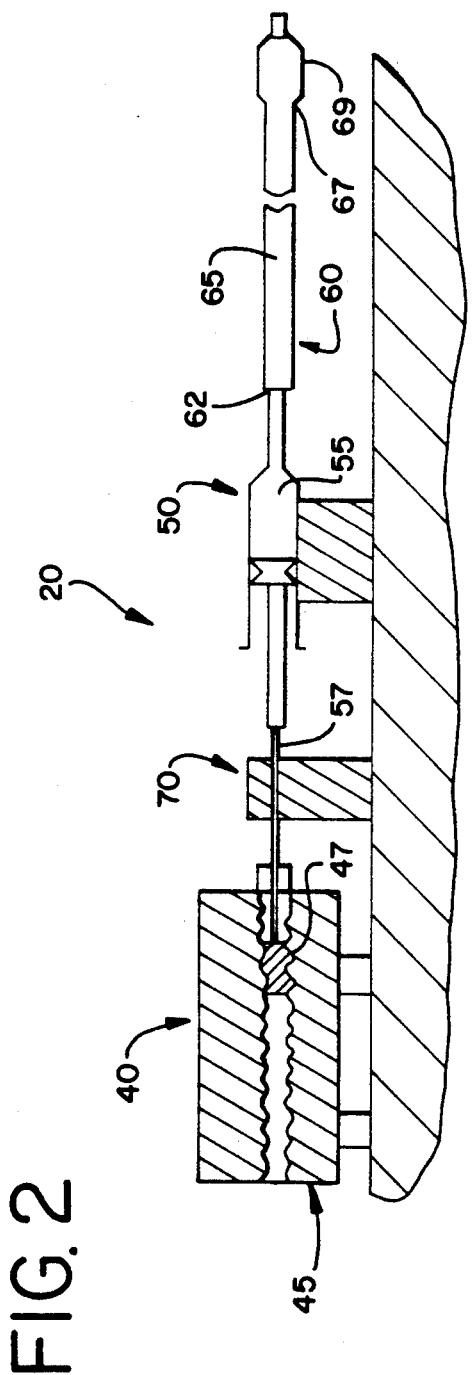
FIG. 2 is an elevational view of an exemplary balloon inflation device.

An inflation device within which the present invention can be embodied is generally illustrated schematically in FIG. 1 and generally designated as 20. Device 20 includes a drive mechanism 40, a pump means 50, and a catheter assembly 60.

Rather than the conventional, manually-actuated approach to balloon angioplasty, one embodiment of the drive mechanism 40 includes a motor 45—which responds to signals received from a microprocessor unit 90 connected to the drive mechanism through conventional interconnection means 80—and by which the pump means 50 can be accurately actuated. An example of such a motor is a conventional high-resolution stepper motor, such as the one manufactured by a Compumotor, 1179 N. McDowell Blvd., Petaluma, Calif. A stepper motor typically delivers power in a large number of small increments thereby providing greater control than in other types of motors. For example, a typical stepper motor provides 150,000 steps to cover a full piston stroke. Depending on the signals received, the microprocessor unit 90 may cause the motor 45 to advance, and thereby cause the pump means 50 connected to the drive mechanism 40 to deliver or withdraw fluid. A suitable microprocessor unit 90 includes an International Business Machines personal computer ("IBM PC"). Suitable conventional interconnection means 80 includes a PC21 interface card made by Compumotor (identified above) through which directions may be communicated from the microprocessor unit 90 to the drive mechanism 40.

The pump means 50 includes any means by which a volume of fluid, such as biocompatible saline solution, or radiopaque dye, contained within the pump means 50 may be delivered to or withdrawn from a known catheter assembly 60. Such means 50 may include a piston and cylinder or syringe assembly 55 having a precision ground piston slidably captured and sealed within a cylinder whose inner diameter is similarly precision-ground. Suitable means 50 may include a syringe pump manufactured by the Harvard Corporation, 22 Pleasant Street, South Natick, Mass. Accurate delivery or withdrawal of a volume of fluid is accordingly possible. The pump means 50 may be cooperatively connected through a hollow shaft 57 to a ball screw 47 included in the drive mechanism 40.

The pump means 50 opens onto and is joined generally to a proximal end 62 of a catheter assembly 60 with which percutaneous transluminal coronary angioplasty (PTCA) is conventionally performed. The catheter 65 included within catheter assembly 60 typically is an elongated, flexible tubular member made from a biocompatible plastic material such as silicone, polyurethane, nylon, PET, polyethylene, and/or polyvinylchloride. Affixed at or near a distal end 67 of the catheter assembly 60 is an angioplasty balloon 69. The balloon 69 may be formed from a suitable material such as synthetic plastic which distends and is able to sufficiently withstand internal pressure to accomplish the dilatation of vascular stenosis or other condition without rupturing. The balloon 69 may be sealingly attached to the outer surface of the catheter 65, such as through ultrasonic or heat bonding.

The microprocessor unit 90 is connected to a system data and control bus in a conventional manner. Input ports and output ports of the system bus allow the unit 90 to interface with the drive mechanism 40 and a monitor 70. The microprocessor unit 90 includes a read only memory (ROM) or the like which is preprogrammed with the necessary control functions to inflate and deflate the treatment balloon 69 according to a pattern that is appropriate for the patient's medical condition and/or to accomplish the dilatation of the afflicted vascular tissue or the like. A random access memory (RAM), or the like, is provided for the temporary storage of data, such as the actual pressure conditions developed within the balloon as quantified by and communicated from the monitoring means 70 through conventional interconnection means 85 to the microprocessor unit 90.

Further different from conventional balloon angioplasty assemblies—in the balloon of which the actual fluid conditions, such as pressure, may only be estimated—the present invention includes monitoring means 70. The monitoring means 70 may include means by which the pressure developed within the balloon may be measured, such as a conventional torque measuring device, or, more specifically, a pressure feedback transducer included within the drive mechanism 40 and interposed between the motor 45 and the pump means 50 or a conventional pressure transducer diaphragm. A suitable pressure monitor is manufactured by Validyne Engineering Corporation, 8626 Wilbur Ave., Northridge, Calif. Data quantified by the monitoring means 70 is transferred, such as through the conventional interconnection means 85, to the microprocessor unit 90 and inputted into its RAM. Suitable interconnection means 85 includes a RS232 digital output connected to a RS232 port included with, for example, the IBM PC. The data communicated to the microprocessor 90 is compared with the expected fluid conditions preprogrammed within the ROM. Where a deviation or deviations between expected fluid conditions and actual fluid conditions are detected, orders appropriate to correct the deviation are communicated through the interconnection means 80 to the drive mechanism 40, which responds appropriately. Such appropriate responses may include actuating the pump means 50 to deliver or withdraw a volume of fluid to increase or decrease the pressure within the balloon 69.

In use, the catheter 65 typically is routed percutaneously through an appropriate entry point, such as the femoral artery, and transluminally positioned so that the balloon 69 affixed to the distal end 67 of the catheter 65 is juxtaposed with a stenotic lesion or other obstruction. Once the balloon 69 is in position, control of the drive mechanism 40 and thereby the pump means 50 may be transferred to the microprocessor unit 90. According to a predetermined pattern programmed within the ROM of the unit 90, the drive mechanism 40 may be actuated thereby causing the pump means 50 to dispense a volume of fluid into the proximal end 62 of the catheter 65. This increase in the amount of fluid present in the catheter 65 increases the hydraulic force present in the catheter 65 causing a resultant increase in the pressure within and a radial expansion of the angioplasty balloon 69.

Figure 3:
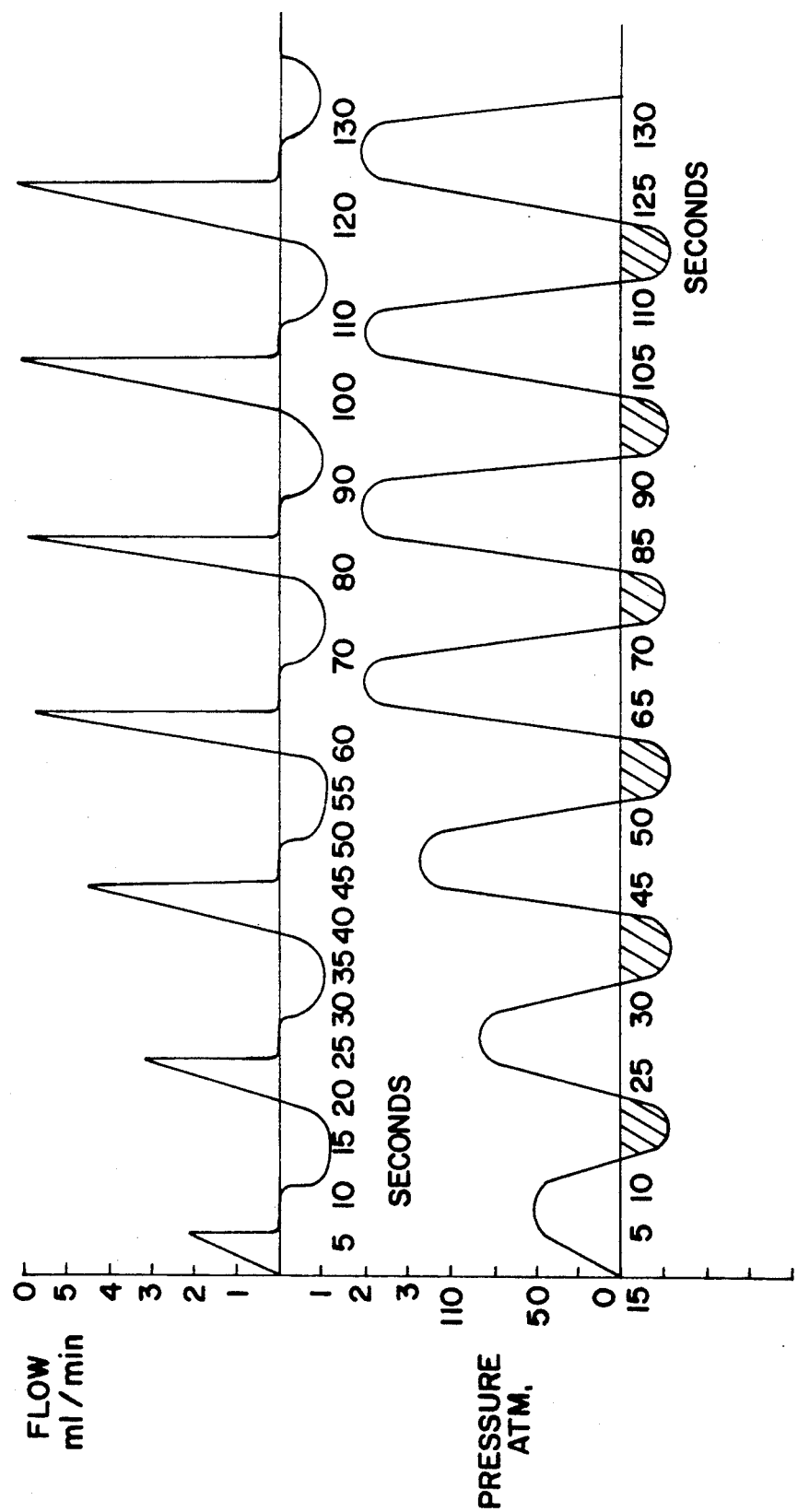
FIG. 3 shows related separate plots of flow (ml./min.) of fluid to or from an angioplasty balloon versus time (seconds) and a plot of the pressure (atmospheres) developed and corresponding to the same flow in the same angioplasty balloon versus time (seconds).

FIG. 3 illustrates, in part, the flow pattern which the control signals programmed in a representative ROM may produce. As illustrated, the flow of fluid into the catheter 65 and ultimately the balloon 69 may increase to a predetermined maximum rate, thereafter decreasing to zero.

The pressure within the balloon responds according to the fluid flow. As shown also in FIG. 3, at time equals zero and in response to no fluid flow, the balloon is essentially evacuated. With time and the introduction of volumes of fluid into the catheter and the balloon 69, the pressure responsively increases. When the fluid flow drops to zero, the pressure remains constant. In response to the pressure exerted upon it by the balloon 69 as expanded, the vascular stenosis or the like compresses. Advantageously, to avoid the prolonged stoppage of blood flow to sites distal to the balloon 69 as expanded, the microprocessor unit 90 signals, according to the pattern programmed within the ROM, the drive mechanism 40 to cause the pump means 50 to withdraw fluid from the proximal end 62 of the catheter 65. This outward flow of fluid results in a reduction in the pressure within and a decrease in the radial size of the balloon 69. Blood flow returns between the partially or wholly evacuated balloon 69 and the vascular wall. Accordingly, with the present invention, an angioplasty balloon may be intermittently pressurized, held at that pressure for a limited period of time, and then depressurized, thereby allowing the blood to flow intermittently to sites distal to the balloon. Data regarding the fluid conditions developed within the balloon 69 during its pressurization and depressurization at any one time may be quantified by the monitoring means 70 and communicated to the microprocessor unit 90 for better control of the drive mechanism 40. By avoiding the conventional prolonged stoppage of the patient's blood flow to sites distal to the balloon 69, the likelihood that angina (muscle cramp), a heart attack, arrythmia or the like due to rhythm disturbance during the angioplasty procedure will be greatly reduced.

Additional embodiments of the present invention include means by which unanticipated changes in the fluid conditions within the balloon 69 may be identified. For example, each balloon 69 generally has known expansion characteristics and carrying capacity. As a result, the flow of fluid to or from the balloon produces an expected pressure within the balloon. However, when, for example, the balloon has or develops leakage, the actual pressure developed within the balloon will deviate from the expected pressure. To detect such variances, the microprocessor unit 90 may include a ROM routine within ROM 96 which, during periods of no flow to and therefore constant pressure in the balloon, will compare the actual pressure within the balloon with a profile of the expected pressure. If variance is detected, appropriate corrective orders may be sent to the drive mechanism 40, such as to cease operation. A further embodiment of the present invention may include a microprocessor unit 90 having logic within the ROM 96 by which the volume of the balloon 69 may be calculated and compared with the pressure within the balloon to determine the actual radial change of the balloon. Corrections to avoid the rupturing of the balloon 69 or blood vessel may be transmitted to the drive mechanism 40. Another embodiment of the invention is a totally hydraulic or pneumatic system where pressure regulators, pilot valves, and flow valves set the pressure and flow rates. Conventional air logic circuitry may be used with or without a microprocessor controller.

It will be understood that the embodiments of the present invention which have been described are merely illustrative of a few of the applications of the principles of the present invention. Numerous modifications may be made by those skilled in the art without departing from the true spirit and scope of the invention.

I claim:
1. A device for the controlled opening of partially or wholly intraluminally blocked biologic passageways, said device comprising:
   balloon means for dilating blockage of vasculature and other biologic passageways, said balloon attached to a generally distal end of a catheter;
   said device increasing and decreasing the radial size of the balloon according to a predetermined pattern which prevents prolonged cessation of blood flow to distal sites of the biologic passageway;
   pump means for dispensing to and withdrawing fluid from said balloon through said catheter;
   a drive mechanism for causing said pump means to dispense and withdraw fluid from said balloon for increasing and decreasing, respectively, the radial size of said balloon;
   monitoring means for identifying actual pressure conditions developed within said balloon positioned in general alignment with the blockage, said monitoring means including a pressure monitor having a pressure feedback transducer interposed between said drive mechanism and said pump means;
   microprocessor means;
   interconnection means for transmitting orders from said microprocessor and transmitting information from said monitoring means; and
   said microprocessor including means for controlling the drive mechanism according to said predetermined pattern, said controlling logic means including additional logic means for evaluating information transmitted from said monitoring means through said interconnection means as to the actual pressure conditions developed within the balloon, said controlling logic means further containing corrective logic means for comparing the actual pressure conditions with the predetermined pattern and generating appropriate corrective orders for actuating said drive mechanism when differences between the expected pressure conditions and the actual pressure conditions are identified, whereby said controlling logic means automatically assures that said predetermined pattern is adhered to.

2. The balloon inflation device according to claim 1, wherein said pump means includes a piston and cylinder syringe assembly connected to a generally proximal end of said catheter.

3. The balloon inflation device according to claim 1, wherein said drive mechanism includes a motor by which said pump means can be accurately actuated.

4. The balloon inflation device according to claim 3, wherein said motor is a stepper motor.

5. The balloon inflation device according to claim 1, wherein said microprocessor includes a personal computer.

6. The balloon inflation device according to claim 1 wherein said microprocessor includes ports, through one of said ports information from said monitoring means through said interconnection means can be transmitted to said microprocessor.

7. The balloon inflation device according to claim 1, wherein said interconnection means includes an interface card by which said microprocessor transmits orders through said interconnection means to said drive mechanism.

8. The balloon inflation device according to claim 1, wherein said microprocessor includes added logic for determining the actual radial change of the balloon.

* * * * *